United States Patent [19]

DeRuiter

[11] Patent Number: Plant 5,820

[45] Date of Patent: Dec. 9, 1986

[54] RUIMEVA ROSE PLANT

[75] Inventor: Gijsbert DeRuiter, Hazerwoude, Netherlands

[73] Assignee: Carlton Rose Nurseries, Carlton, Oreg.

[21] Appl. No.: 692,503

[22] Filed: Jan. 18, 1985

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Chernoff, Vilhauer, McClung, Birdwell & Stenzel

[57] ABSTRACT

A vigorous rose plant of the Hybrid Tea Class obtained as a seedling from a seed parent of the Varlon variety and a pollen parent of the Meigerion variety provides abundant long lasting orange blooms, which maintain their true color from bud through leaf petal, on a continuous basis in a greenhouse.

15 Drawing Figures

BACKGROUND AND SUMMARY OF THE INVENTION

The present invention relates to a new and distinct variety of Hybrid Tea rose plant, a seedling resulting from a definite effort to produce an improvement in this class of rose. The object of the present invention is to provide a hardy rose plant of the Hybrid Tea class which is capable of freely yielding quality cut flowers under greenhouse conditions.

The primary features of this new variety which connotate its distinctive advance over previously existing types are its vigorous growth, its orange-red color, its ability under greenhouse conditions to freely yield a quantity of cut flowers which maintain true color after being cut, from bud through petal drop, and its long vase life.

The variety of rose plant of the present invention was obtained at Hazerwoude, The Netherlands, as a seedling from a seed parent of the Varlon variety and a pollen parent of the Meigerion variety. The crossing was made during July, 1977, the sowing during March, 1978, and the first flower appeared during July, 1978.

Asexual reproduction of this new and distinctive variety shows that its unique combination of characteristics come true to form and is established and transmitted through succeeding propagations by grafting and by budding.

BRIEF DESCRIPTION OF THE DRAWINGS

In the accompanying photographs typical specimens of the vegetative growth and flowers of the new variety are shown in different stages of development and are depicted in color as nearly true as is reasonably possible to make the same in color illustrations of this character:

FIG. 1 shows a young shoot.

FIG. 2 shows a young shoot with flower bud formed.

FIG. 3 shows a flower bud with sepals breaking loose.

FIG. 5 shows a flower ¾ open (side view).

FIG. 6 shows a flower ¾ open (top view).

FIG. 15 shows a composite of several flowers in different stages of development from nearly open to full flower.

DETAILED DESCRIPTION OF THE DISCLOSURE

Figures 4, 7, 8, 9, 10, 11, 12, 13, 14:
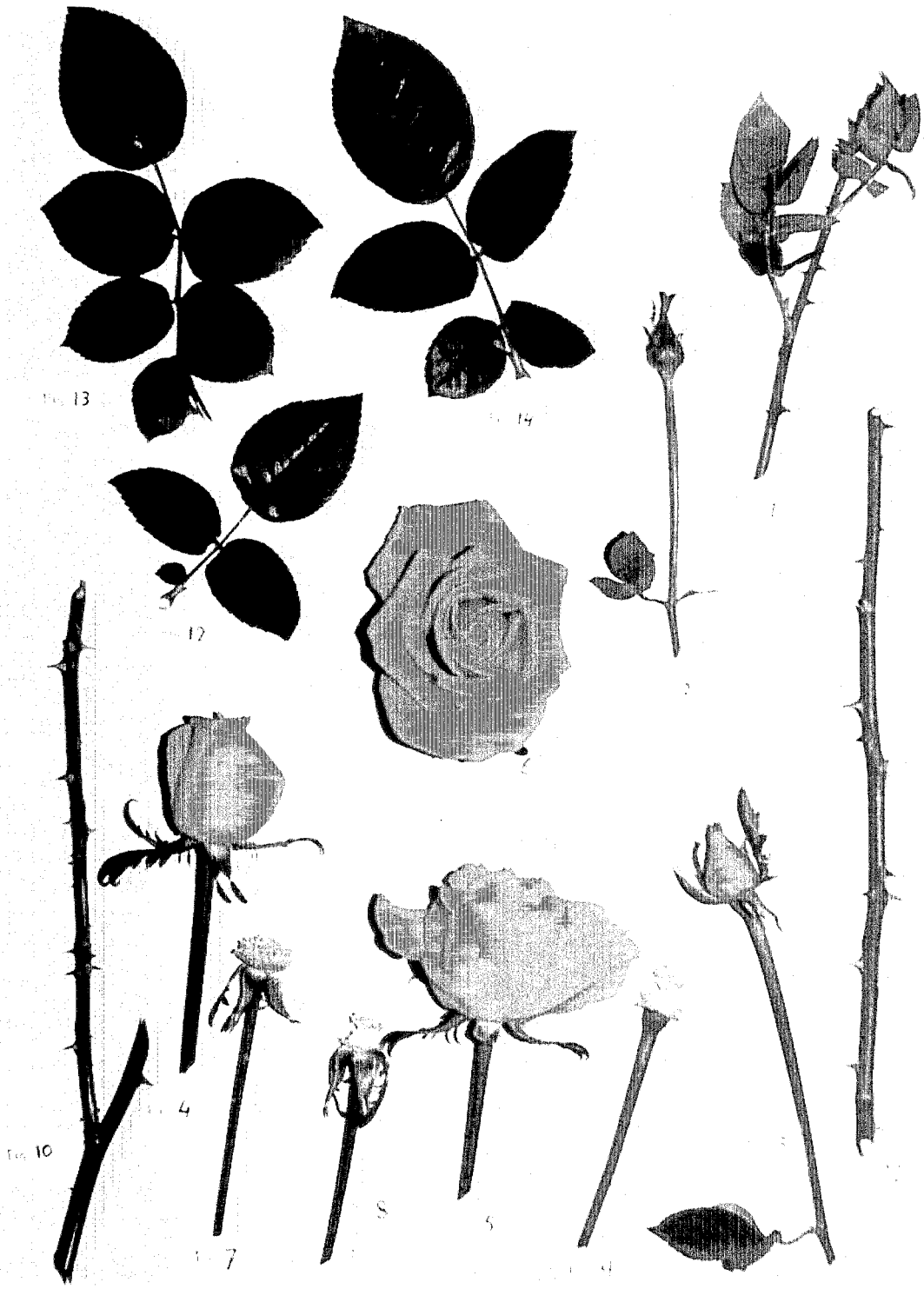
FIG. 4 shows a flower bud in cutting stage with sepals down.
FIG. 7 shows a flower with its petals removed showing the arrangement of stamens.
FIG. 8 shows a flower with its petals and stamens removed, showing the pistils.
FIG. 9 shows a flower with its petals, stamens, and sepals removed showing the pistils and receptacle.
FIG. 10 shows a stem with normal branching.
FIG. 11 shows a normal cut flower wood with leaves removed showing thorn pattern and eyes.
FIG. 12 shows a normal three leaflet leaf showing the stipules.
FIG. 13 shows a normal compound leaf showing six leaflets.
FIG. 14 shows a normal compound leaf showing five leaflets and the rachis of typical foliage.

The following description was made during September, 1981 of the rose plants of the new and distinct variety growing in a greenhouse at Hazerwoude, The Netherlands. Color designations are to Munsell A Limit Color Cascade.

FLOWER

Flowers borne: Singly to stems on long, strong stems.

Quantity of bloom: Abundant in greenhouse.

Continuity: Continuous.

Fragrance: Slight; tea.

Bud:

*Peduncle.*—Medium length; medium weight; erect; medium green; almost smooth,

*Before calyx breaks.*—Size: medium. Form: pointed with a conspicuous neck; with out foliaceous appendages on the surface of the bud; with little foliaceous parts extending beyond the tip of the bud equal to ¼ of its length.

*As calyx breaks.*—Color: 39-10.

*As first petal opens.*—Size: Large. Color: Outside: 40-10. Inside: 35-12. Opening: It does open up well.

Bloom:

*Size when fully open.*—Large: 3½ inches to 4½ inches.

*Petalage.*—Double; from 26 to 30 petals; arranged regularly.

*Form.*—High centered at first; becoming open centered; petals remaining at first tightly cupped inward; becoming later at maturity rolled outward.

Petals: Leathery; with inside velvety; outside satiny.

Shape:

*Outer.*—Round, with one notch.

*Intermediate.*—Round; with one tooth.

*Inner.*—Round; with one notch.

Color:

*Color of newly opened flower.*—Outer petal: Outside surface: 40-10. Inside surface: 37-12. Intermediate petal: Outside surface: 40-10. Inside surface: 38-11. Inner petal: Outside surface: 40-11.3. Inside surface: 38-11.

*Color of flower 3 days after opening.*—Outer petal: Outside surface: 39-10.5. Inside surface: 37-11. Inner petal: Outside surface: 40-11.3. Inside surface: 38-11.

*General color effect.*—Newly opened flower: Bright satiny evenly colored flower. Flowers three days open: Bright, velvety evenly colored flower, fading purple.

Behavior: Drop off cleanly.

Flower longevity: Cut roses grown in greenhouse kept at livingroom temperature for 10 days during September.

REPRODUCTIVE ORGANS

Stamens: Many; arranged regularly about pistils.

Filaments: Many; most without anthers; medium length. Color: 39-14.

Anthers: All open at once; medium size. Color: 29-8. Seldom fused with a petaloid.

Pollen: Moderate amount; yellow.

Pistils: Many.

Styles: Uneven; medium length; thin thickness; bunched.

Stigma: Yellow.

Ovaries: All enclosed.

Hips: Very globular; smooth; moderately fleshy walls; reddish.

Sepals: Permanent; moderately long; spear-shaped.

Seeds: Medium number; large.

PLANT

Foliage:

*Leaves.*—Compound of 3 and 5 leaflets; moderately abundant; large size; leathery; glossy.

*Leaflet.*—Shape: oval; apex acute; base margin simply serrate. Color: Mature upper surface: 21-14.5. Mature under surface: 23-11.5. Young upper surface: 35-15. Young under surface: 41-15.

*Rachis.*—Medium. Upper side: smooth. Under side: sparsely prickly.

*Stipules.*—Short length; medium width; with short points; turning out at an angle of less then 45 degrees; recurved toward the stem.

*Disease.*—Resistance comparable to the average variety growing under the same cultural conditions.

GROWTH

Habit: Upright; branched.

Growth: Vigorous.

Canes: Moderately heavy.

Main stems: Dull.

*Color.*—22-14.

*Prickles.*—None.

*Hairs.*—None.

Branches: Dull.

*Color.*—22-14.

*Prickles.*—Several.

*Color.*—26-13.

*Hairs.*—None.

New shoots:

*Prickles.* —*Several.*

*Color.*—29-15.

*Hairs.*—None.

What is claimed is:

1. A new and distinct variety of rose plant of the Hybrid Tea Class obtained as a seedling from a seed parent of the Varlon class and a pollen parent of the Meigerion variety, characterized by its vigorous growth, its orange-red color, its ability to yield on a continuous basis in a greenhouse large long lasting blooms which maintain true color after being cut from bud through petal drop, substantially as shown and described.

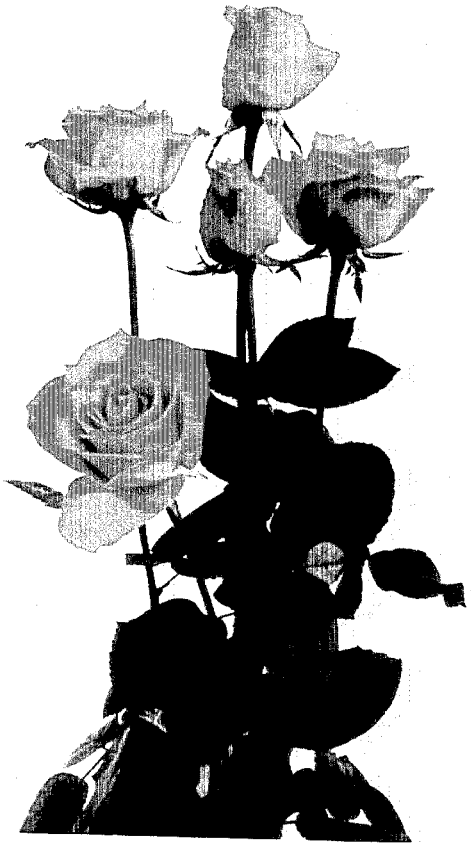

* * * * *